US010993703B2

(12) United States Patent
Kimoto

(10) Patent No.: US 10,993,703 B2
(45) Date of Patent: May 4, 2021

(54) ULTRASOUND DIAGNOSIS APPARATUS AND COMPUTER READABLE RECORDING MEDIUM

(71) Applicant: Konica Minolta, Inc., Tokyo (JP)

(72) Inventor: Takashi Kimoto, Yokohama (JP)

(73) Assignee: KONICA MINOLTA, INC., Tokyo (JP)

( * ) Notice: Subject to any disclaimer, the term of this patent is extended or adjusted under 35 U.S.C. 154(b) by 728 days.

(21) Appl. No.: 15/704,552

(22) Filed: Sep. 14, 2017

(65) Prior Publication Data

US 2018/0085097 A1    Mar. 29, 2018

(30) Foreign Application Priority Data

Sep. 23, 2016  (JP) .............................. JP2016-185043

(51) Int. Cl.
*G06F 3/048*     (2013.01)
*A61B 8/00*      (2006.01)
(Continued)

(52) U.S. Cl.
CPC ................ *A61B 8/54* (2013.01); *A61B 8/461* (2013.01); *A61B 8/467* (2013.01); *A61B 8/468* (2013.01);
(Continued)

(58) Field of Classification Search
CPC ....... G06F 3/0481–0489; G06F 1/1626; G06F 1/1652; G06F 1/20; G06F 1/16;
(Continued)

(56) References Cited

U.S. PATENT DOCUMENTS 7,555,728 B2 * 6/2009 Esaki ................... G06F 3/04845
715/824
8,063,887 B2 * 11/2011 Barrus ................... G06F 1/3203
345/173
(Continued)

FOREIGN PATENT DOCUMENTS

| CN | 102228383 A | 11/2011 |
| JP | 2014150804 A | 3/2012 |
| WO | 2016/147460 A1 | 9/2016 |

OTHER PUBLICATIONS

CNIPA, Office Action for the corresponding Chinese patent application No. 20171010853595.9, dated Mar. 25, 2020, with English translation.
(Continued)

*Primary Examiner* — Steven B Theriault
(74) *Attorney, Agent, or Firm* — Lucas & Mercanti, LLP

(57) ABSTRACT

An ultrasound diagnosis apparatus generates an ultrasound image based on a reception signal obtained by an ultrasound probe to display the ultrasound image in a display, the reception signal being of ultrasound transmitted from the ultrasound probe toward an inside of a subject and reflected at the inside of the subject. The apparatus includes: an image display controller that causes the display to display at least one operable image indicating a target of a contact operation in a touch panel provided so as to overlaid on a screen of the display; and a processor that carries out predetermined processing corresponding to the operable image as the target of the contact operation in response to the contact operation in the touch panel. The processor skips the predetermined processing corresponding to a predetermined operable image among the operable image if a predetermined operation limit condition is satisfied.

12 Claims, 7 Drawing Sheets

(51) Int. Cl.
  *A61B 8/08*     (2006.01)
  *G06F 3/0488*   (2013.01)
(52) U.S. Cl.
  CPC .......... *A61B 8/5207* (2013.01); *A61B 8/5223* (2013.01); *G06F 3/04886* (2013.01)
(58) Field of Classification Search
  CPC .... G06F 1/1616; G06F 1/1618; G06F 1/1637; G06F 1/1681; G06F 1/1684; G06F 2200/201; G06F 2203/04105; G06F 3/0446; G06F 3/046; A61B 8/54; A61B 8/468; A61B 8/5223; A61B 8/5207; A61B 8/461; A61B 8/52; A61B 2034/107; A61B 34/20; A61B 34/10; A61B 2090/365; A61B 2034/105; A61B 2034/2065; A61B 34/25; A61B 2090/378; A61B 90/361; A61B 2090/374; A61B 90/39; A61B 2090/3983; A61B 2090/364; A61B 2017/00207; A61B 2034/2074; A61B 5/742; A61B 8/469; A61B 5/7425; G16H 50/30
  See application file for complete search history.

(56) References Cited

U.S. PATENT DOCUMENTS

| | | | | |
|---|---|---|---|---|
| 8,228,347 | B2* | 7/2012 | Beasley | A61B 8/00 345/665 |
| 8,303,502 | B2* | 11/2012 | Washburn | A61B 8/00 600/424 |
| 8,400,548 | B2* | 3/2013 | Bilbrey | G06F 1/1694 348/333.01 |
| 8,532,596 | B1* | 9/2013 | Park | G06F 3/04883 455/158.4 |
| 8,681,108 | B2* | 3/2014 | Aono | G06F 3/04886 345/173 |
| 8,717,327 | B2* | 5/2014 | Hering | G06F 3/0416 345/156 |
| 8,951,200 | B2* | 2/2015 | Mo | A61B 8/469 600/443 |
| 9,207,859 | B2* | 12/2015 | Woo | G06F 3/04815 |
| 9,361,002 | B2* | 6/2016 | Enkerud | G06F 3/0484 |
| 9,414,810 | B2* | 8/2016 | Dunkan | A61B 8/4438 |
| 9,520,154 | B2* | 12/2016 | Lee | H04N 5/2624 |
| 9,538,985 | B2* | 1/2017 | Mander | A61B 8/4427 |
| 9,552,153 | B2* | 1/2017 | Lee | G06F 3/04883 |
| 9,652,589 | B2* | 5/2017 | Caspi | G06F 19/321 |
| 9,710,098 | B2* | 7/2017 | Xiong | G06F 3/0416 |
| 9,733,826 | B2* | 8/2017 | Zhang | G06F 3/04883 |
| 9,804,707 | B2* | 10/2017 | Durojaiye | G06F 3/0418 |
| 9,870,721 | B2* | 1/2018 | Savitsky | A61B 8/466 |
| 9,877,699 | B2* | 1/2018 | Chiang | G16H 30/20 |
| 9,898,122 | B2* | 2/2018 | Dao | G06F 1/1626 |
| 10,019,081 | B2* | 7/2018 | Buchanan | G06F 3/038 |
| 10,070,844 | B2* | 9/2018 | Mander | A61B 8/5207 |
| 10,089,633 | B2* | 10/2018 | Thiyagarajan | G06Q 30/016 |
| 10,133,467 | B2* | 11/2018 | Ma | G06F 3/04817 |
| 10,134,125 | B2* | 11/2018 | Mauldin, Jr. | A61B 8/5246 |
| 10,142,764 | B2* | 11/2018 | Lim | H04L 67/34 |
| 10,159,468 | B2* | 12/2018 | Yoo | A61B 8/5223 |
| 10,209,816 | B2* | 2/2019 | Park | G06F 3/0416 |
| 10,265,052 | B2* | 4/2019 | Song | A61B 8/0883 |
| 10,285,666 | B2* | 5/2019 | Yang | A61B 8/523 |
| 10,331,334 | B2* | 6/2019 | Paek | G06F 3/04883 |
| 10,368,836 | B2* | 8/2019 | Merritt | A61B 5/743 |
| 10,420,533 | B2* | 9/2019 | Kim | A61B 8/467 |
| 10,445,051 | B1* | 10/2019 | Subash | G06F 3/0482 |
| 10,456,111 | B2* | 10/2019 | Lee | G01S 7/52033 |
| 10,613,637 | B2* | 4/2020 | Goetz | G06F 3/017 |
| 10,631,825 | B2* | 4/2020 | Lee | A61B 8/468 |
| 10,705,649 | B2* | 7/2020 | Li | G06F 3/0412 |
| 2003/0071850 | A1* | 4/2003 | Geidl | G06F 3/04883 715/781 |
| 2004/0196255 | A1* | 10/2004 | Cheng | G06F 3/0488 345/104 |
| 2004/0207661 | A1* | 10/2004 | Akaki | A61B 8/463 715/764 |
| 2006/0242607 | A1* | 10/2006 | Hudson | G06F 3/04817 715/863 |
| 2007/0242056 | A1* | 10/2007 | Engelhardt | G06F 3/04883 345/173 |
| 2007/0285439 | A1* | 12/2007 | King | G09G 5/397 345/638 |
| 2008/0123912 | A1* | 5/2008 | Lal | G06T 5/20 382/128 |
| 2008/0208047 | A1* | 8/2008 | Delso | A61B 8/469 600/437 |
| 2009/0021475 | A1* | 1/2009 | Steinle | G06F 19/00 345/156 |
| 2009/0043195 | A1* | 2/2009 | Poland | A61B 8/461 600/437 |
| 2009/0147325 | A1* | 6/2009 | Fujiwara | H04N 1/603 358/505 |
| 2009/0174679 | A1* | 7/2009 | Westerman | G06F 3/04883 345/173 |
| 2010/0145195 | A1* | 6/2010 | Hyun | A61B 8/467 600/437 |
| 2010/0182247 | A1* | 7/2010 | Petschnigg | G06F 1/1647 345/173 |
| 2010/0321324 | A1* | 12/2010 | Fukai | A61B 8/467 345/173 |
| 2010/0323762 | A1* | 12/2010 | Sindhu | G06F 1/1613 455/566 |
| 2011/0012849 | A1* | 1/2011 | Cho | G06F 1/3203 345/173 |
| 2011/0043434 | A1* | 2/2011 | Roncalez | A61B 8/467 345/3.1 |
| 2011/0069021 | A1* | 3/2011 | Hill | G06F 3/0416 345/173 |
| 2011/0072368 | A1* | 3/2011 | Macfarlane | G01C 21/32 715/760 |
| 2011/0175827 | A1* | 7/2011 | Bogue | G06F 3/0416 345/173 |
| 2011/0208052 | A1* | 8/2011 | Entrekin | G16H 15/00 600/437 |
| 2011/0246916 | A1* | 10/2011 | Leskela | G06F 3/0488 715/765 |
| 2011/0264709 | A1* | 10/2011 | Beardsmore | G06F 9/451 707/804 |
| 2011/0273388 | A1* | 11/2011 | Joo | G06F 3/0488 345/173 |
| 2011/0288696 | A1* | 11/2011 | Lefebure | A63H 30/04 701/2 |
| 2012/0036429 | A1* | 2/2012 | Ajima | G06Q 30/02 715/259 |
| 2012/0075290 | A1* | 3/2012 | Kurosaki | G06T 15/10 345/419 |
| 2012/0179039 | A1* | 7/2012 | Pelissier | H04N 19/61 600/443 |
| 2012/0179997 | A1* | 7/2012 | Miyazaki | G06F 3/0482 715/830 |
| 2012/0262407 | A1* | 10/2012 | Hinckley | G06F 3/04883 345/173 |
| 2012/0274574 | A1* | 11/2012 | Aono | G06F 3/0488 345/173 |
| 2012/0306749 | A1* | 12/2012 | Liu | G06F 3/0488 345/163 |
| 2012/0306927 | A1* | 12/2012 | Lee | G06F 3/041 345/660 |
| 2012/0313865 | A1* | 12/2012 | Pearce | G06F 3/0416 345/173 |
| 2013/0147787 | A1* | 6/2013 | Ignatchenko | H04N 21/4312 345/419 |
| 2013/0151999 | A1* | 6/2013 | Seul | G06F 3/048 715/762 |
| 2013/0154983 | A1* | 6/2013 | Christiansson | G06F 3/04166 345/173 |
| 2013/0263002 | A1* | 10/2013 | Park | G11B 27/34 715/719 |

(56) References Cited

U.S. PATENT DOCUMENTS

| | | | | |
|---|---|---|---|---|
| 2013/0324850 A1* | 12/2013 | Petruzzelli | | A61B 8/465 600/443 |
| 2013/0338960 A1* | 12/2013 | Bourgault | | G06F 9/451 702/122 |
| 2014/0015782 A1* | 1/2014 | Kim | | G06K 9/00422 345/173 |
| 2014/0018708 A1* | 1/2014 | Dunbar | | A61B 34/25 601/2 |
| 2014/0035942 A1* | 2/2014 | Yun | | G06F 1/1637 345/592 |
| 2014/0059486 A1* | 2/2014 | Sasaki | | A61B 8/465 715/810 |
| 2014/0068503 A1* | 3/2014 | Yoon | | G06F 3/04842 715/790 |
| 2014/0104189 A1* | 4/2014 | Marshall | | G06F 3/0488 345/173 |
| 2014/0164965 A1* | 6/2014 | Lee | | G06F 3/04842 715/765 |
| 2014/0221835 A1* | 8/2014 | Ota | | A61B 8/54 600/443 |
| 2014/0325402 A1* | 10/2014 | Jung | | G06F 3/04883 715/763 |
| 2014/0365319 A1* | 12/2014 | Huang | | G06F 3/0484 705/14.73 |
| 2014/0372881 A1* | 12/2014 | Aikawa | | G06F 40/166 715/268 |
| 2014/0372938 A1* | 12/2014 | Park | | G06F 3/0488 715/793 |
| 2015/0005630 A1* | 1/2015 | Jung | | G06F 19/321 600/437 |
| 2015/0054761 A1* | 2/2015 | Kim | | G06F 3/017 345/173 |
| 2015/0145820 A1* | 5/2015 | Huang | | G06F 3/04883 345/174 |
| 2015/0265247 A1* | 9/2015 | Roh | | A61B 8/465 600/438 |
| 2015/0297179 A1* | 10/2015 | Mander | | A61B 8/5207 600/440 |
| 2015/0301707 A1* | 10/2015 | Tasnadi | | G06F 3/0485 715/771 |
| 2016/0073987 A1* | 3/2016 | Ohashi | | A61B 6/465 378/62 |
| 2016/0106394 A1* | 4/2016 | Kang | | G06F 3/0482 600/437 |
| 2016/0113626 A1* | 4/2016 | Lee | | A61B 5/0035 600/440 |
| 2016/0157825 A1* | 6/2016 | Lee | | A61B 8/5223 600/437 |
| 2016/0170632 A1* | 6/2016 | Zhang | | G06F 3/04886 345/173 |
| 2016/0357388 A1* | 12/2016 | Paine | | G06F 3/041661 |
| 2017/0102846 A1* | 4/2017 | Ebler | | A61M 1/3626 |
| 2017/0119352 A1* | 5/2017 | Anand | | A61B 8/463 |
| 2017/0124700 A1* | 5/2017 | Sarojam | | A61B 8/46 |
| 2017/0357371 A1* | 12/2017 | Kim | | G06F 3/0446 |
| 2018/0052963 A1* | 2/2018 | Eguchi | | A61B 8/4427 |
| 2019/0129558 A1* | 5/2019 | Yildiz | | G06F 3/04886 |

OTHER PUBLICATIONS

JPO, Office Action for the corresponding Japanese patent application No. 2016-185043, dated May 26, 2020, with English translation.

* cited by examiner

FIG.11

| DIAGNOSIS TARGET | ARRANGEMENT PATTERN OF OPERATION OBJECT BUTTONS |
|---|---|
| ABDOMINAL SITE | PATTERN A |
| OBSTETRIC SITE | PATTERN B |
| GYNECOLOGIC SITE | PATTERN B |
| THYROID SITE | PATTERN C |
| CAROTID ARTERY | PATTERN D |
| ORTHOPEDIC SITE | PATTERN E |

ULTRASOUND DIAGNOSIS APPARATUS AND COMPUTER READABLE RECORDING MEDIUM

CROSS-REFERENCE TO RELATED APPLICATIONS

The present U.S. patent application claims a priority under the Paris Convention of Japanese Patent Application No. 2016-185043 filed on Sep. 23, 2016, the entirety of which is incorporated herein by references.

BACKGROUND

Technological Field

The present invention relates to an ultrasound diagnosis apparatus and a computer readable recording medium.

Description of the Related Art

Heretofore, these has been known an ultrasound diagnosis apparatus that includes an ultrasound probe radiating ultrasound toward an inside of a subject to receive a reflected wave from the subject, processes a resulting signal to generate an ultrasound image corresponding to the internal structure of the subject, and displays the ultrasound image on a display to provide diagnosis information on the internal structure of the subject. Such ultrasound diagnosis apparatus or non-invasive diagnosis apparatus is also used for clinical treatment.

Some ultrasound diagnosis apparatuses include touch panels overlaid on the screen of displays and can carry out various processing in response to operations to the touch panels (for example, refer to Japanese Patent Application Laid-Open Publication No. 2014-150804). Such ultrasound diagnosis apparatuses can carry out predetermined processing in response to ready and intuitive input operations. This can enhance the efficiency of diagnosis and reduce the operation load on operators.

In diagnosis using the ultrasound diagnosis apparatus, diagnosis information is often confirmed and explained while referring to ultrasound images appearing on the displays. Thus, known ultrasound diagnosis apparatuses are prone to false operations due to unintentional contact with the touch panels.

SUMMARY

An object of the present invention is to provide an ultrasound diagnosis apparatus that can prevent false operation due to unintentional contact with the touch panel and a computer readable recording medium.

To achieve at least one of the abovementioned objects, according to an aspect of the present invention, these is provided an ultrasound diagnosis apparatus reflecting one aspect of the present invention which generates an ultrasound image based on a reception signal obtained by an ultrasound probe to display the ultrasound image in a display, the reception signal being of ultrasound transmitted from the ultrasound probe toward an inside of a subject and reflected at the inside of the subject, the apparatus including: an image display controller that causes the display to display at least one operable image indicating a target of a contact operation in a touch panel provided so as to overlaid on a screen of the display; and a processor that carries out predetermined processing corresponding to the operable image as the target of the contact operation in response to the contact operation in the touch panel, wherein the processor skips the predetermined processing corresponding to a predetermined operable image among the operable image if a predetermined operation limit condition is satisfied.

According to another aspect of the present invention, these is provided a computer readable recording medium reflecting one aspect of the present invention which stores a program, the medium being readable by a computer provided in an ultrasound diagnosis apparatus which generates an ultrasound image based on a reception signal obtained by an ultrasound probe to display the ultrasound image in a display, the reception signal being of ultrasound transmitted from the ultrasound probe toward an inside of a subject and reflected at the inside of the subject, the program causing the computer to function as: an image display controller that causes the display to display at least one operable image indicating a target of a contact operation in a touch panel provided so as to overlaid on a screen of the display; and a processor that carries out predetermined processing corresponding to the operable image as the target of the contact operation in response to the contact operation in the touch panel, wherein the processor skips the predetermined processing corresponding to a predetermined operable image among the operable image if a predetermined operation limit condition is satisfied.

BRIEF DESCRIPTION OF THE DRAWINGS

The advantages and features provided by one or more embodiments of the invention will become more fully understand from the detailed description given hereinbelow and the appended drawings which are given by way of illustration only, and thus are not intended as a definition of the limits of the present invention:

FIG. 11 illustrates an example setting of arrangement patterns of operable buttons for different diagnosis targets according to the fourth modification.

DETAILED DESCRIPTION OF EMBODIMENTS

Hereinafter, one or more embodiments of the present invention will be described with reference to the drawings. However, the scope of the invention is not limited to the disclosed embodiments.

An ultrasound diagnosis apparatus and a computer readable recording medium according to embodiments of the present invention will now be described with reference to the accompanying drawings.

Figure 1:
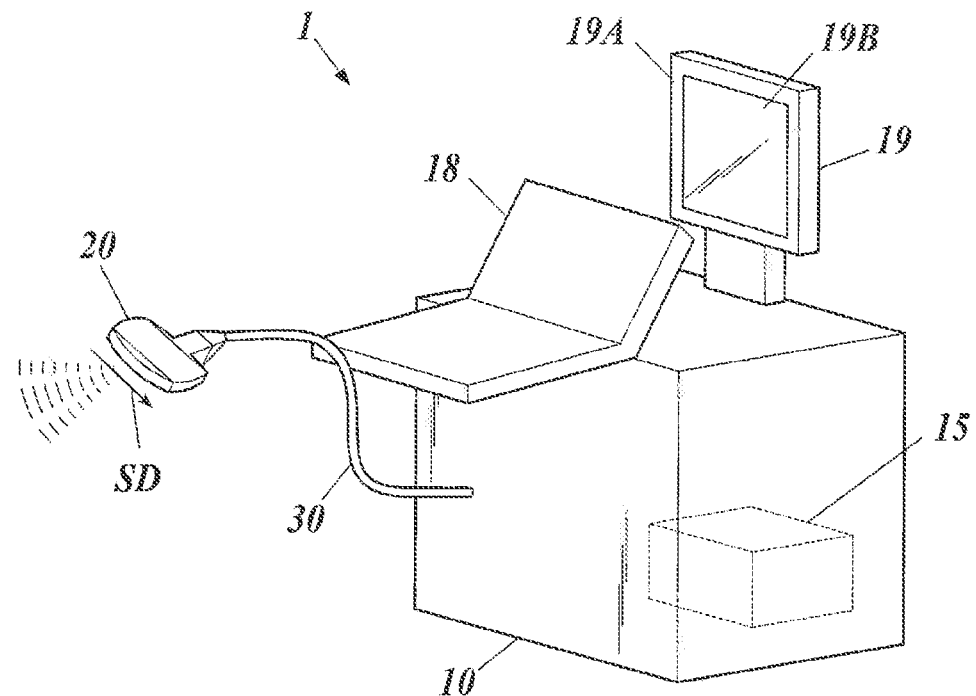
FIG. 1 illustrates an overall configuration of an ultrasound diagnosis apparatus.

FIG. 1 illustrates the overall configuration of the ultrasound diagnosis apparatus 1 according to an embodiment of the present invention.

Figure 2:
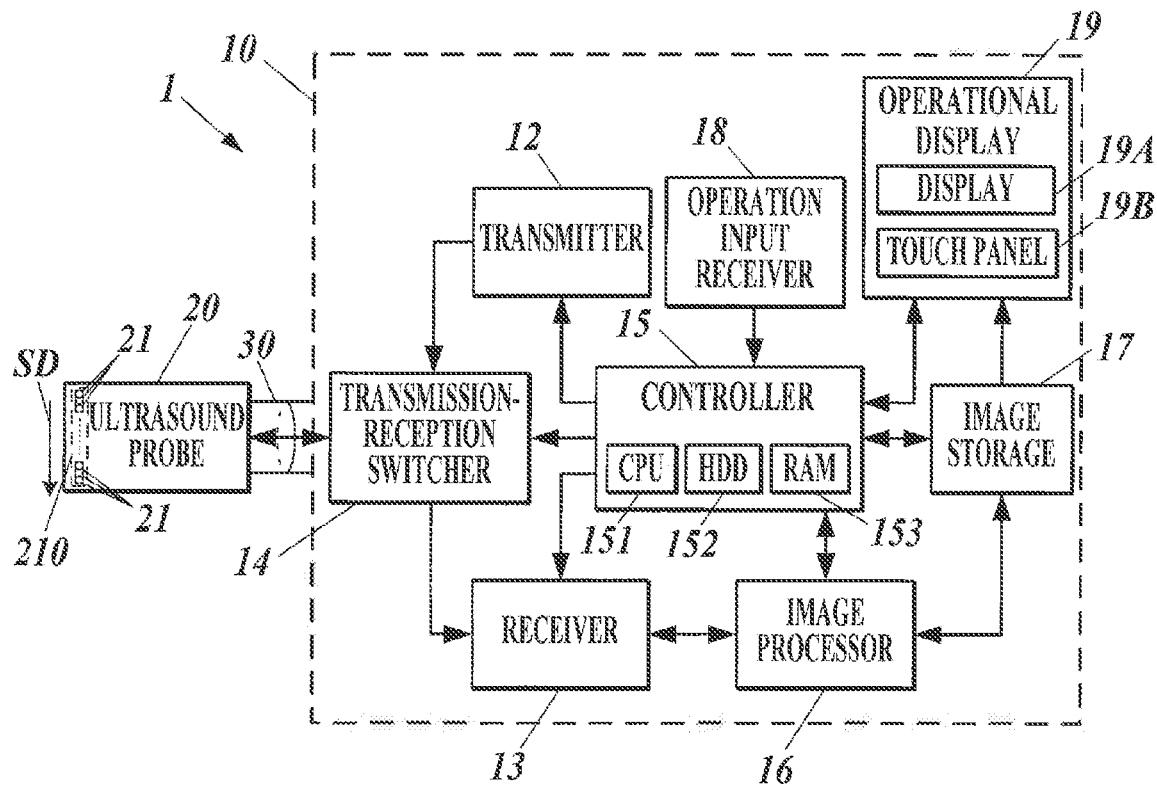
FIG. 2 is a block diagram illustrating an essential functional configuration of the ultrasound diagnosis apparatus.

FIG. 2 is a block diagram illustrating the essential functional configuration of the ultrasound diagnosis apparatus 1.

With reference to FIG. 1, the ultrasound diagnosis apparatus 1 includes an ultrasound diagnosis apparatus body 10 and an ultrasound probe 20 connected to the ultrasound diagnosis apparatus body 10 with a cable 30. The ultrasound diagnosis apparatus body 10 includes a controller 15 (including an image display controller, a processor, a trajectory display controller, a storage controller, and a computer), an operation input receiver 18, and an operational display 19 including a display 19A and a touch panel 19B. The controller 15 sends driving signals to the ultrasound probe 20 to instruct the ultrasound probe 20 to radiate ultrasound in response to an input operation of an input device, such as a keyboard or a mouse, of the operation input receiver 18 by an operator or a contact operation of the operator on the touch panel 19B of the operational display 19. The controller 15 also receives reception signals upon reception of ultrasounds from the ultrasound probe 20, carries out various processing, and causes the results to appear on the display 19A, if required.

With reference to FIG. 2, the ultrasound diagnosis apparatus body 10 includes a transmitter 12, receiver 13, transmission-reception switcher 14, controller 15, image processor 16, image storage 17, operation input receiver 18, and operational display 19.

The transmitter 12 outputs pulsed signals (driving signals) to the ultrasound probe 20 in accordance with control signals input from the controller 15, to cause ultrasounds to be generated at the ultrasound probe 20. The transmitter 12 includes, for example, a clock generator circuit, a pulse generator circuit, a pulse-width determiner, and a delay circuit. The clock generator circuit generates clock signals that determine the transmission timings of the pulsed signals and the transmission frequency. The pulsed generator circuit generates bipolar rectangular pulses having predetermined voltage amplitude at a predetermined cycle. The pulse-width determiner determines the pulse width of the rectangular pulses output from the pulse generator circuit. The rectangular pulses generated at the pulse generator circuit are separated to different wiring routes for each of the transducers 21 of the ultrasound probe 20 before or after input to the pulse-width determiner. The delay circuit delays the generated rectangular pulses in accordance with the transmission timings to the transducers 21 by delay times set for the respective wiring routes.

The receiver 13 receives reception signals from the ultrasound probe 20 in accordance with the control of the controller 15. The receiver 13 includes, for example, an amplifier, an A/D converter circuit, and a phase regulating adder. The amplifier amplifies the reception signals corresponding to the ultrasounds received by the transducers 21 of the ultrasound probe 20 by a predetermined amplification rate. The A/D converter circuit convers the amplified reception signals to digital data by a predetermined sampling frequency. The phase regulating adder regulates the time phase of the A/D converted reception signals through addition of delay times to the respective wiring routes corresponding to the respective transducers 21, and performs addition (phase regulation addition) the resulting signals to generate sound ray data.

The transmission-reception switcher 14 switches, on the basis of the control of the controller 15, between a transmission mode where driving signals are sent from the transmitter 12 to the transducers 21 for causing the transducers 21 to oscillate ultrasounds, and a reception mode where reception signals are output to the receiver 13 when signals of the ultrasounds emitted from the transducers 21 are obtained.

The controller 15 includes a central processing unit (CPU) 151, a hard disk drive (HDD) 152 (storage), and a random access memory (RAM) 153. The CPU 151 reads various programs stored in the HDD 152 (computer readable recording medium), loads the various programs to the RAM 153, comprehensively controls the operation of components of the ultrasound diagnosis apparatus 1 in accordance with the loaded programs. The HDD 152 stores control programs and various processing programs for operation of the ultrasound diagnosis apparatus 1, various configuration data, and image files generated by the ultrasound diagnosis apparatus 1. The programs and the configuration data may be stored in an updatable manner in an auxiliary storage including a non-volatile memory, such as a flash memory, besides the HDD 152. The RAM 153 is a volatile memory, such as SRAM and DRAM. The RAM 153 provides a work memory space for the CPU 151 and stores temporary data.

Besides the CPU 151 of the controller 15, the image processor 16 carries out calculation for generation of ultrasound images (diagnosis images) based on the received data on the ultrasounds. The ultrasound images include image data appearing on the operational display 19 at substantially real time, a series of moving data, and still image data of snapshots. This calculation may otherwise be carried out by the CPU 151.

The image storage 17 is a volatile memory, such as a dynamic random access memory (DRAM). Alternatively, the image storage 17 may be any non-volatile memory that is rewritable at high speed. The image storage 17 stores image data on ultrasound images in frame unit for real-time display after the image data is processed by the image processor 16. The image data stored in the image storage 17 is read in accordance with the control of the controller 15 and sent to the display 19A or an external device of the ultrasound diagnosis apparatus 1 via a communicator (not shown). In the case where the display mode of the display 19A is a television mode, a digital signal converter (DSC) should be connected to both the image storage 17 and the display 19A to output the image data after conversion of the scanning format.

The operation input receiver 18 includes a push-button switch, a toggle switch, a keyboard, a mouse, or a track ball, or a combination of two or more of these. The operation input receiver 18 converts the input operation by the operator to operation signals and sends these operation signals to the controller 15.

The display 19A of the operational display 19 is a liquid crystal display (LCD), an organic electroluminescent (EL) display, an inorganic EL display, a plasma display, or a cathode ray tube (CRT) that includes a display screen and a driver that drives the display 19A. The display 19A generates driving signals of the display screen (each display pixel) in accordance with the control signals from the CPU 151 and the image data generated by the image processor 16 and displays menus and statuses pertaining to ultrasound diagnosis, operation buttons (operable images) that are to receive contact operation on the touch panel 19B, and measurement data, such as ultrasound images based on the received ultrasounds, on the display screen.

The touch panel 19B of the operational display 19 is a capacitance touch panel that overlays the display screen of the display 19A. The touch panel 19B detects contact based on a variation in the capacitance across the internal conductive film and the surface due to contact of, for example, a finger of an operator to the surface, and sends an operation signal indicating the detected position (coordinates) to the controller 15. Beside the capacitance touch panel, the touch panel 19B may be a resistive touch panel or an electromagnetic induction touch panel.

The operation input receiver 18 and the operational display 19 may be integrated with the casing of the ultrasound diagnosis apparatus body 10 or may be attached from the outside of the ultrasound diagnosis apparatus body 10 via an USB cable or the like. If the ultrasound diagnosis apparatus body 10 is provided with operation input terminals and display output terminals, known peripheral devices, such as operating devices and display devices, may be connected to these terminals and be used in place of the operation input receiver 18 and the operational display 19.

In FIG. 1, the operation input receiver 18 and the operational display 19 are provided separately. Alternatively, they may be provided integrally. For example, the operation button and the track ball of the operation input receiver 18 may be disposed on the casing of the operational display 19 including the display 19A and the touch panel 19B.

The ultrasound probe 20 functions as an acoustic sensor that oscillates ultrasounds (approximately 1 to 30 MHz) to transmit (emit) the ultrasounds to a subject, such as a living body, and that receives the reflected wave (echoes), i.e. the ultrasounds reflected at the subject, to convert the received waves into electrical signals. The ultrasound probe 20 includes a transducer array 210 of the transducers 21 transmitting and receiving ultrasounds.

The transducer array 210 is an array of the transducers 21, each including a piezoelectric device including a piezoelectric body and electrodes disposed at the two ends of the piezoelectric body where charges are generated by deformation (expansion and contraction) of the piezoelectric body. The voltage pulses (pulsed signals) applied to the transducers 21 cause the piezoelectric bodies to deform in accordance with the electric fields generated at the respective piezoelectric bodies and oscillate ultrasounds. Ultrasounds of a predetermined frequency band incident on the transducers 21 vary the thicknesses of the piezoelectric bodies (vibrate the piezoelectric bodies) due to acoustic pressure. This causes electric charges in accordance with the variation of the thickness to appear at the two ends of each piezoelectric body in the direction of the variation. This induces electric charges corresponding to the electric charges generated at the piezoelectric bodies at the electrodes disposed at the two ends of the respective piezoelectric devices. The piezoelectric bodies are ferroelectric bodies.

The ultrasound probe 20 according to this embodiment includes the transducer array 210 including a one-dimensional array of 192 transducers 21 in a predetermined transducer array direction. Alternatively, the transducers 21 may also be disposed in a direction orthogonal to the transducer array direction in a two-dimensional array. Any number of transducers 21 may be provided. The ultrasound probe 20 according to this embodiment transmits ultrasounds from a group of consecutive transducers 21 (for example, 64 transducers 21) among the 192 transducers 21 based on the pulsed signals from the transmitter 12. The group of the transducers 21 transmitting the ultrasounds are shifted by a predetermined number of transducers 21 in the transducer array direction every time ultrasounds are generated, to carry out scanning in a scanning direction SD parallel to the transducer array direction. In this embodiment, the ultrasound probe 20 is of a convex electronic scanning type having a sectoral transmission range of ultrasounds transmitted at different timings. Alternatively, the ultrasound probe 20 may be of any scanning type including various types of electronic scanning, such as linear electronic scanning and sector electronic scanning, and various types of mechanical scanning, such as linear scanning, sector scanning, arc scanning, and radial scanning. The received frequency of ultrasounds of the ultrasound probe 20 may be set to any bandwidth.

The ultrasound diagnosis apparatus body 10 of the ultrasound diagnosis apparatus 1 can be connected to an ultrasound probe 20 selected from multiple ultrasound probes 20 suitable for different diagnosis targets.

The cable 30 has a connector (not shown) at one end for connection with the ultrasound diagnosis apparatus body 10. The ultrasound probe 20 is detachably connected to the ultrasound diagnosis apparatus body 10 through the cable 30.

The various processing and operations carried out in response to contact operations of the touch panel 19B of the ultrasound diagnosis apparatus 1 according to this embodiment will now be described.

When an examination with the ultrasound diagnosis apparatus 1 is started, a menu screen (not shown) is displayed for receiving input operations for designating a target site of a subject (a person in this embodiment) from an operator. Upon designation of the target site through the contact operation of the touch panel 19B, the ultrasound probe 20 begins transmission and reception of ultrasounds in accordance with the setting corresponding to the designated target site. Image data on ultrasound images reflecting the internal structure of the subject is generated based on the reception signals from the ultrasound probe 20, and an ultrasound diagnosis screen including the ultrasound images appears on the display 19A. The ultrasound diagnosis screen includes the ultrasound images and multiple operable buttons (operable images) that receive contact operations on the touch panel 19B.

Figure 3:
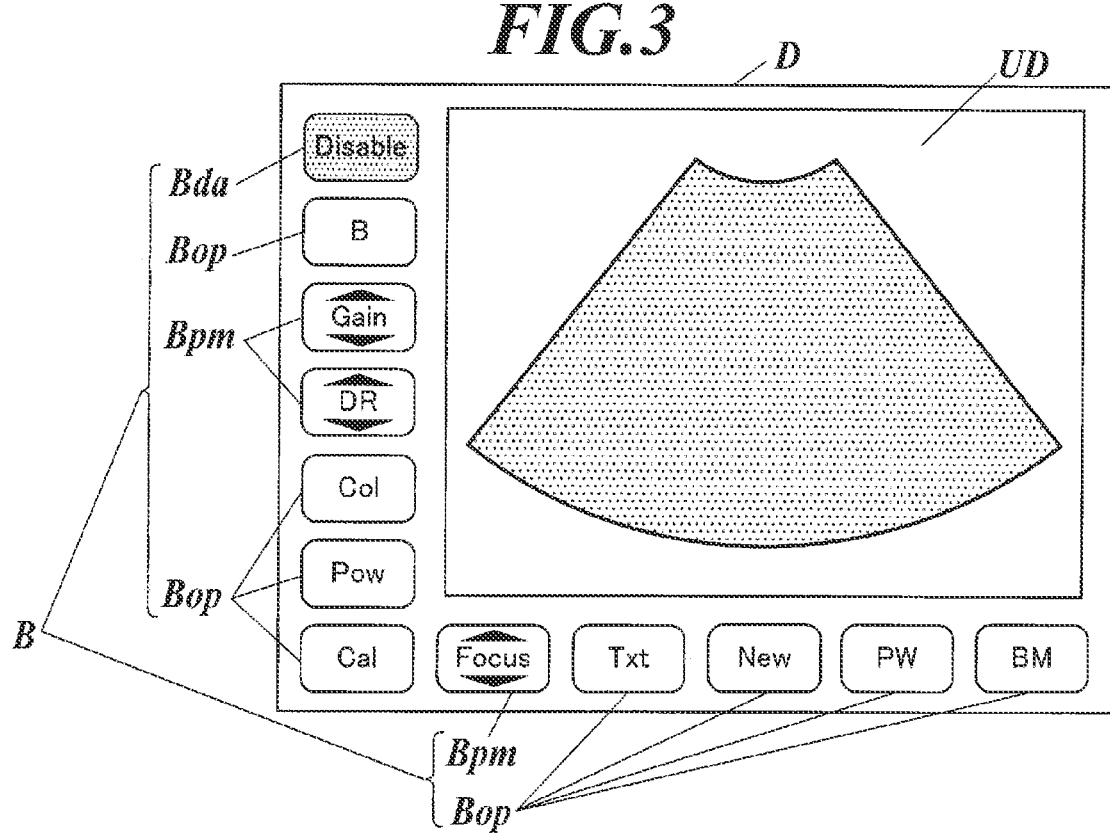
FIG. 3 illustrates an example ultrasound diagnosis screen.

FIG. 3 illustrates an example ultrasound diagnosis screen D.

The ultrasound diagnosis screen D includes multiple (12 in FIG. 3) operable buttons B disposed in an L shape along the left edge and the bottom edge of the screen and an ultrasound image UD appearing in a rectangular area other than the area in which the operable buttons B are disposed. The operable buttons B include an operation limit button Bda (operation limit image) that is operated to limit or disable contact operations of the touch panel 19B, operation buttons Bop that are operated to instruct the ultrasound diagnosis apparatus 1 to perform predetermined operations and configuration modifications, and parameter adjustment buttons Bpm that are operated to adjust the parameters involving the processing of driving signals for the transmission of ultrasounds and reception signals of ultrasounds.

The operation limit button Bda, which indicated by the characters "Disable," is disposed at the upper left corner of the ultrasound diagnosis screen D, as illustrated in FIG. 3. The processing carried out when the operation limit button Bda receives a contact operation will be described in detail below.

The ultrasound diagnosis screen D illustrated in FIG. 3 further includes eight operation buttons Bop: "B," "Col," "Pow," "Cal," "Txt," "New," "PW," and "BM."

The "B" operation button Bop is operated to display the ultrasound image UD in a B mode in which the intensity of the reception signal is represented by brightness.

The "Col" operation button Bop is operated to display the ultrasound image UD through a color doppler scheme in which the moving rate and direction of the target area are represented by color.

The "Pow" operation button Bop is operated to display the ultrasound image UD through a power doppler scheme in which the absolute value of the moving rate of the target area is represented by color.

The "Cal" operation button Bop is operated to enter a measuring mode in which the distance between two points in the ultrasound image is measured.

The "Txt" operation button Bop is operated to enter a text input mode in which text is input onto the ultrasound image.

The "New" operation button Bop is operated to start new examination processing.

The "PW" operation button Bop is operated to display the ultrasound image UD through a power doppler scheme in which the moving rate of a target at a predetermined position is determined through transmission and reception of pulsed waves by the same transducers 21.

The "BM" operation button Bop is operated to display a body mark on the ultrasound image UD. The body mark is, for example, an image including a graphic representation of the body of a subject including various sites and a probe mark disposed at a position corresponding to the target site in the graphic representation and indicating the orientation of the ultrasound probe 20 at the target site (probe direction).

The ultrasound diagnosis screen D in FIG. 3 includes three parameter adjustment buttons Bpm: "Gain," "DR," and "Focus."

The "Gain" parameter adjustment button Bpm is operated to adjust the level of reception signals such that the range of the reception signals reflected in the display of the ultrasound image UD becomes appropriate.

The "DR" parameter adjustment button Bpm is operated to adjust the range of the level of reception signals reflected in the display of the ultrasound image UD.

The "Focus" parameter adjustment button Bpm is operated to adjust the focus depth of the transmitted ultrasounds.

The ultrasound image UD in the ultrasound diagnosis screen D is a diagnosis image representing the internal structure of the target through, for example, a brightness distribution and is an operable image like the operable buttons B that is to receive contact operations through the touch panel 19B. In specific, upon contact operations of the ultrasound image UD, the predetermined processing is executed in this embodiment. Although any processing may be assigned to the ultrasound image UD, freeze processing and freeze cancel processing are assigned in this embodiment. The freeze processing pauses the ultrasound image UD that is updated every time ultrasounds are transmitted and displayed in substantially real time (moving image display), and displays the paused image (still image display). The freeze cancel processing switches the still image display to the moving image display. Any processing may be assigned to the ultrasound image UD, for example, any processing involving the operational settings of the ultrasound diagnosis apparatus 1 or the adjustment of the ultrasound images, such as the processing for entering the measuring mode described above or the processing for entering the text input mode.

The operation performed in response to a contact operation of the operation limit button Bda will now be described.

If a predetermined operation limit condition is satisfied, the ultrasound diagnosis apparatus 1 according to this embodiment operates in an operation limit mode in which contact operations of the touch panel 19B are limited through predetermined means. In this embodiment, a contact operation of the operation limit button Bda satisfies the operation limit condition and thus causes the ultrasound diagnosis apparatus 1 to enter the operation limit mode. In the descriptions below, the operational mode other than the operation limit mode is referred to as normal mode.

Figure 4:
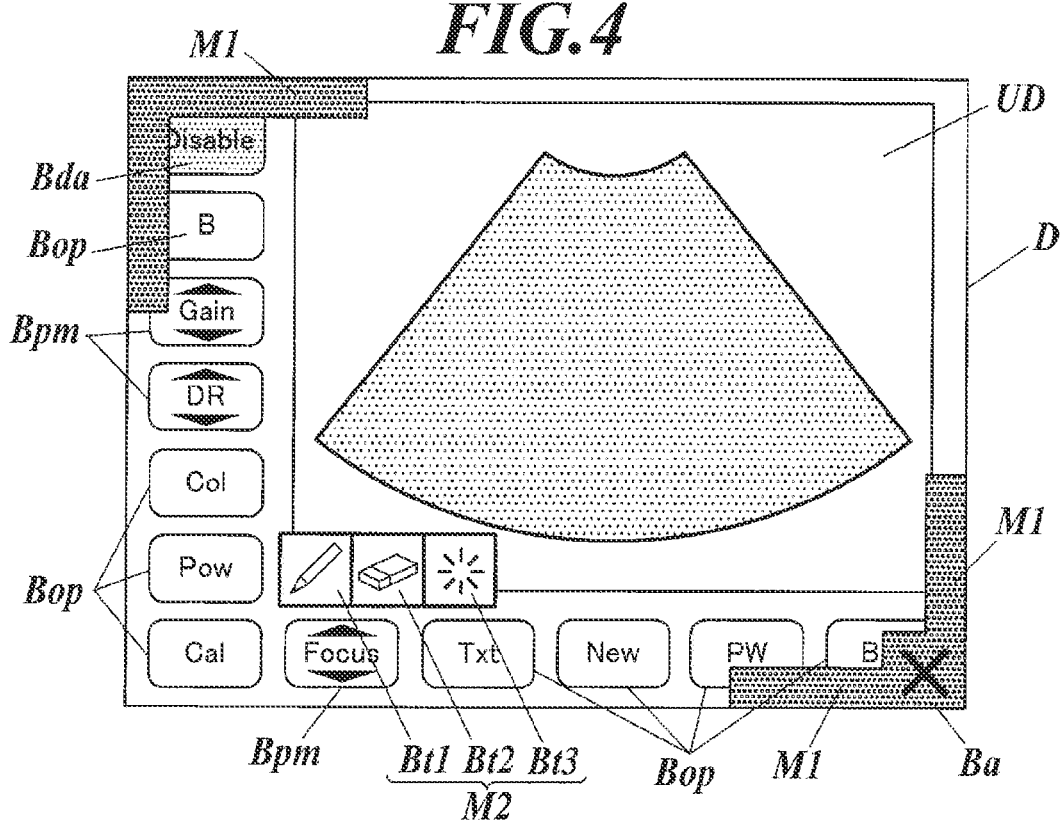
FIG. 4 illustrates an example ultrasound diagnosis screen in an operation limit mode.

FIG. 4 illustrates an example ultrasound diagnosis screen D in the operation limit mode.

In the operation limit mode, L-shaped operation-limit identification marks M1 (operation-limit identification images) appear at the upper left and lower right corners along the external edges of the ultrasound diagnosis screen D, and an operation limit cancel button Ba (operation limit cancel image) including an X mark overlays the operation-limit identification mark M1 at the lower right corner of the ultrasound diagnosis screen D. Trajectory-processing-state identification marks M2, which are to be described below, are appears near the lower left corner of the ultrasound image UD.

The ultrasound diagnosis apparatus 1 in the operation limit mode disables any contact operation of the operable buttons B and the ultrasound image UD. That is, even if the operable buttons B and the ultrasound image UD receive contact operations, the processing correlated to the operable buttons B and the ultrasound image UD is skipped.

In the operation limit mode, the operation-limit identification marks M1 and the operation limit cancel button Ba appear on the ultrasound diagnosis screen D, to inform the operator of the rescission of the contact operations of the operable buttons B and the ultrasound image UD, as described above.

A contact operation of the operation limit cancel button Ba in the operation limit mode ends the operation limit mode because the operation limit condition is no longer satisfied. Upon the end of the operation limit mode, the ultrasound diagnosis apparatus 1 enters the normal mode in which the operable buttons B and the ultrasound image UD are activated to receive contact operations. Further, the operation-limit identification marks M1, the operation limit cancel button Ba, and the trajectory-processing-state identification mark M2 in the ultrasound diagnosis screen D are deleted, such that the ultrasound diagnosis screen D in FIG. 3 appears on the display 19A.

In the operation limit mode according to this embodiment, the trajectory of the contact operation performed on the touch panel 19B appears on the ultrasound image UD.

Figure 5:
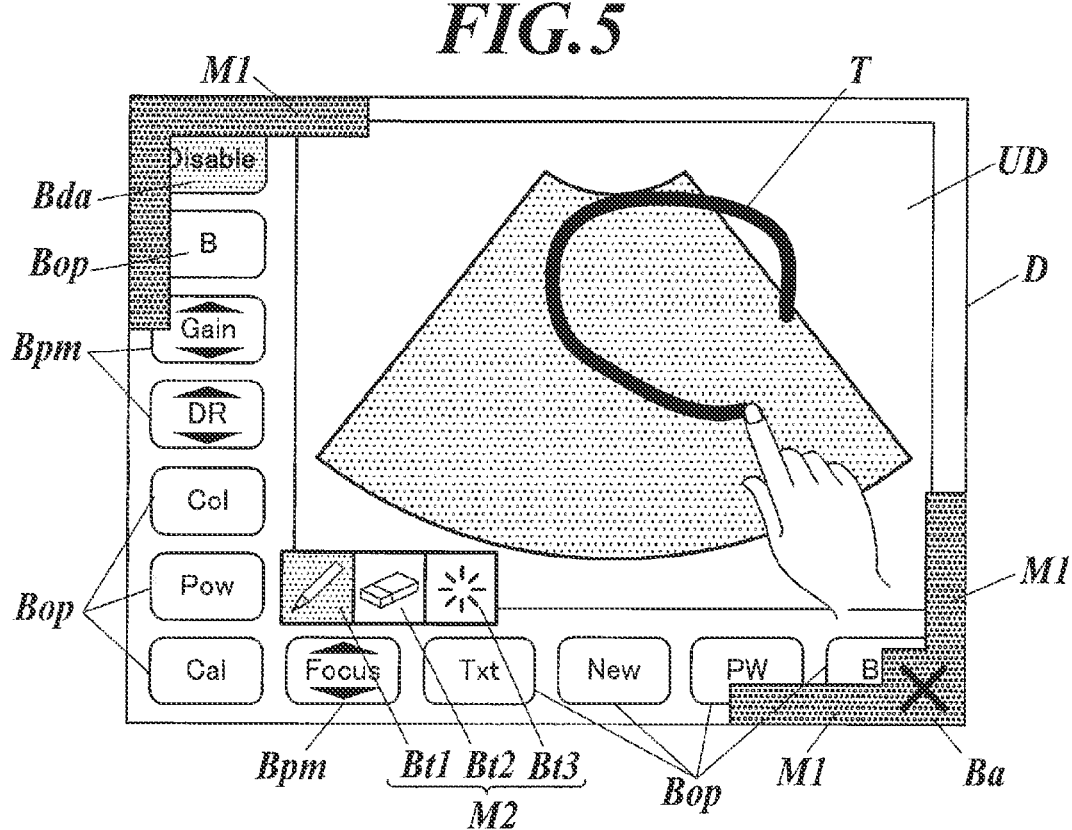
FIG. 5 illustrates an example display of a trajectory in the operation limit mode.

FIG. 5 illustrates an example display of a trajectory in the operation limit mode.

In the operation limit mode, the trajectory-processing-state identification mark M2 near the lower left corner of the ultrasound image UD indicates that the processing involving the display of the trajectory can be carried out. The trajectory-processing-state identification mark M2 includes a trajectory reflection button Bt1 (trajectory-display-state identification image), a partial-trajectory deletion button Bt2 (trajectory deletion image), and a full-trajectory deletion button Bt3 (trajectory deletion image).

The trajectory reflection button Bt1 is operated to enter a trajectory displayable state. A contact operation of the trajectory reflection button Bt1 causes the trajectory reflection button Bt1 to be colored as illustrated in FIG. 5, and enter an activated state in which the trajectory image T is displayed. The trajectory of the contact operation performed to the touch panel 19B in this state appears on the ultrasound diagnosis screen D in the form of a trajectory image T.

The partial-trajectory deletion button Bt2 is operated to delete a designated portion of the displayed trajectory image T. In an activated state of the partial-trajectory deletion button Bt2 caused by a contact operation of the partial-trajectory deletion button Bt2, a portion of the trajectory image T displayed on the ultrasound diagnosis screen D overlapping the trajectory of a contact operation on the touch panel 19B is deleted. That is, a portion of the trajectory image T is deleted as a result of an effect mimicking an eraser moving along the trajectory of the contact operation in the activated state of the partial-trajectory deletion button Bt2.

A contact operation of the trajectory full deletion button Bt3 deletes the entire displayed trajectory image T.

The switching operation between the normal mode and the operation limit mode will now be described. The ultrasound diagnosis apparatus 1 according to this embodiment switches between the normal mode and the operation limit mode. The normal mode carries out various processing based on a single layer image (first layer image) whereas the operation limit mode carries out various processing based on a second layer image overlaid on the first layer image.

Figure 6:
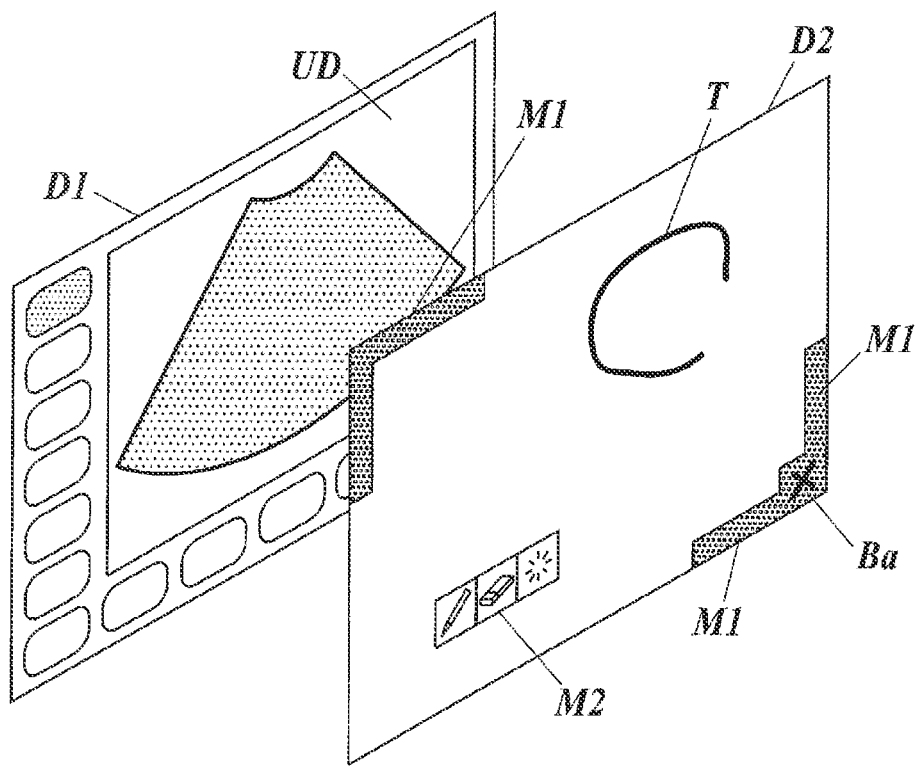
FIG. 6 illustrates layer images constituting the ultrasound diagnosis screen in the operation limit mode.

FIG. 6 illustrates layer images constituting the ultrasound diagnosis screen D in the operation limit mode.

As shown in FIG. 6, the ultrasound diagnosis screen D in the operation limit mode (FIGS. 4 and 5) includes a first layer image D1 and a second layer image D2 overlaid thereon. The first layer image D1 is identical to the ultrasound diagnosis screen D in the normal mode (FIG. 3) including the ultrasound image UD and the various operable buttons B. The second layer image D2 in the operation limit mode includes components to be superposed onto the ultrasound diagnosis screen D in the normal mode (i.e., the first layer image D1), the components including the operation-limit identification marks M1, the operation limit cancel button Ba, the trajectory-processing-condition identification mark M2, and the trajectory image T.

The controller 15 of the ultrasound diagnosis apparatus 1 separately stores the image data on the first layer image D1 and the image data on the second layer image D2 in the HDD 152. In the normal mode, the ultrasound diagnosis screen D in FIG. 3 appears on the display 19A based on the image data on the first layer image D1. In the operation limit mode, the ultrasound diagnosis screen D in FIGS. 5 and 6 appears on the display 19A based on the combined image data on the first and second layer images.

The HDD 152 stores first reference data on the correspondence between the coordinate ranges of the areas occupied by the operable buttons B and the ultrasound image UD in the first layer image D1 and the processing to be carried out in response to contact operations of the coordinate ranges. In response to a contact operation of the touch panel 19B in the normal mode, the coordinates of the contact operation are referenced in the first reference data, and the processing corresponding to the coordinates (i.e., the processing assigned to the operable buttons B and the ultrasound image UD corresponding to the coordinates) is determined and carried out.

The HDD 152 stores second reference data on the correspondence between the coordinate ranges of the areas occupied by the operation limit cancel button Ba and the trajectory-processing-condition identification mark M2 in the second layer image D2 and the processing to be carried out in response to the contact operations of the respective coordinate ranges. In response to a contact operation of the touch panel 19B in the operation limit mode, the coordinates of the contact operation are referenced in the second reference data, and the processing corresponding to the coordinates (i.e., the processes correlated to the operation limit cancel button Ba or the trajectory-processing-condition identification mark M2 corresponding to the coordinates) is determined and carried out. The second reference data does not contain the correspondence between the operable buttons B and the ultrasound image UD in the first layer image D1 and the various processing. Thus, reference to the second reference data does not prompt the processing corresponding to the operable buttons B and the ultrasound image UD even if a contact operation is performed on the operable buttons B and the ultrasound image UD. Thus, the operation limit mode disables the contact operation of the operable buttons B and the ultrasound image UD.

In the operation limit mode, the trajectory of the contact operation to the touch panel 19B is identified, and the image data on the trajectory image T is written over or deleted from the image data on the second layer image D2, depending on the selected status of the trajectory reflection button Bt1 and the partial-trajectory deletion button Bt2 of the trajectory-processing-condition identification mark M2.

In this way, the processing in the normal mode and the operation limit mode can be carried out using different layer images and different sets of reference data on the layer image, to perform operations in accordance with the operational modes through simple processing. The second layer image D2 including the operation-limit identification marks M1, the operation limit cancel button Ba, the trajectory-processing-condition identification mark M2, and the trajectory image T is stored in the form of image data separate from the image data on the first layer image D1 including the ultrasound image UD. This enables storage of the ultrasound image UD without the components of the second layer image D2 through simple processing in response to an input operation by the operator instructing the storage of the ultrasound image UD.

The image file generation processing of generating image files of the ultrasound images UD will now be described.

Figure 7:
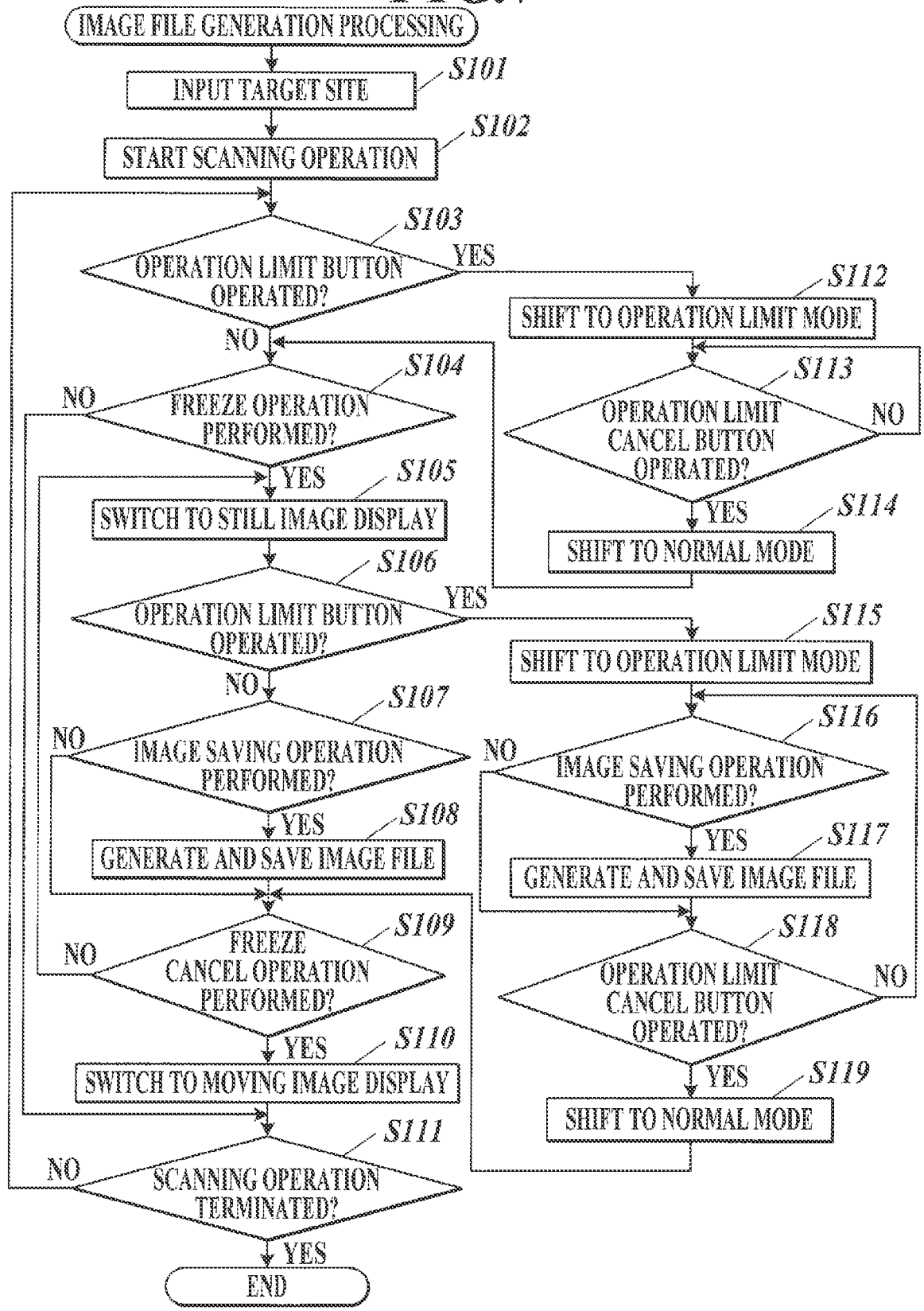
FIG. 7 is a flow chart illustrating controlling steps of an image file generation processing.

FIG. 7 is a flow chart illustrating the control processing of the image file generation processing.

The image file generation processing is carried out for the examination of a predetermined target site with the ultrasound diagnosis apparatus 1.

Upon start of the image file generation processing, the controller 15 carries out the processing involving input of the target site (step S101). In this case, the controller 15 causes a predetermined menu screen that receives an input operation (contact operation) for designating a target site to appear on the display 19A. The controller 15 performs various settings for the target site designated through the input operation. In specific, the controller 15 executes the setting of the scanning operation and the parameters for processing on the reception signals in accordance with the target site and stores the setting in the RAM 153.

Patient information input processing and other processing may be carried out before step S101.

Upon completion of step S101, the controller 15 starts the scanning operation (step S102). In this case, the controller 15 instructs the transmitter 12 to output pulsed signals to the ultrasound probe 20. In response, the ultrasound probe 20 performs ultrasound scanning and transmission. The controller 15 instructs the receiver 13 to receive a reception signal of the waves reflected at the ultrasound probe 20. The controller 15 instructs the image processor 16 to generate the image data on the ultrasound image UD based on the reception signals. The controller 15 stores every frame of the resulting image data in the image storage 17 and instructs the display 19A to display the ultrasound diagnosis screen D including the ultrasound image UD (i.e., the first layer image D1) displayed in real time (moving image display) based on the image data stored in the image storage 17.

The controller 15 performs the scanning operation in accordance with the setting for the target site selected in step S101. The setting of the scanning operation, for example, include the measurement mode and parameters such as the gain and dynamic range for the processing of the reception signals.

In the case of a contact operation of any one of the operable buttons B and the ultrasound image UD during display of the ultrasound diagnosis screen D after the start of the scanning operation, the controller 15 carries out the processing corresponding to the relevant operable button B or ultrasound image UD. That is, the controller 15 references the first reference data on the coordinates of the contact operation and carries out the processing corresponding to the operable button B or ultrasound image UD corresponding to the coordinates.

The controller 15 determines whether a contact operation is performed on the operation limit button Bda (whether the operation limit condition is satisfied) (step S103). That is, if a contact operation is performed on the touch panel 19B and the first reference data on the coordinates corresponding to the contact operation is included in the coordinate range of the operation limit button Bda, the controller 15 determines that a contact operation is performed on the operation limit button Bda.

If it is determined that a contact operation is performed on the operation limit button Bda (YES in step S103), the controller 15 shifts the operational mode of the ultrasound diagnosis apparatus 1 to the operation limit mode (step S112). In specific, the controller 15 causes the ultrasound diagnosis screen D, which is a combined image of the first layer image D1 and the second layer image D2, to appear on the display 19A. A contact operation of the touch panel 19B causes the controller 15 to reference the second reference data on the coordinates of the contact operation and carry out the processing corresponding to the coordinates (in particular, display or deletion of the trajectory image T).

The controller 15 determines whether a contact operation is performed on the operation limit cancel button Ba (in other words, determines whether the operation limit condition is no longer satisfied) (step S113). That is, if the coordinates of the contact operation searched for the second reference data are included in the coordinate range of the operation limit cancel button Ba, the controller 15 determines that a contact operation is performed on the operation limit cancel button Ba. If a contact operation is not performed on the operation limit cancel button Ba (NO in step S113), the controller 15 continues to operate in the operation limit mode and repeats step S113.

If it is determined that a contact operation is performed on the operation limit cancel button Ba (YES in step S113), the controller 15 shifts the operational mode of the ultrasound diagnosis apparatus 1 to the normal mode (step S114). That is, if the ultrasound diagnosis screen D consisting of only the first layer image D1 appears on the display 19A and a contact operation is performed on the touch panel 19B, the controller 15 references the first reference data on the coordinates of the contact operation and carries out the operation corresponding to the coordinates (i.e., corresponding to the relevant operable button B or ultrasound image UD).

If the operational mode shifts to the normal mode in step S114 or if it is determined that no contact operation is performed on the operation limit button Bda in step S103 (NO in step S103), the controller 15 determines whether a contact operation (freeze operation) is performed to instruct freeze processing (step S104). In this case, if a contact operation is performed on the ultrasound image UD, the controller 15 determines that the freeze operation is performed. If it is determined that a freeze operation is performed (YES in step S104), the controller 15 switches the display of the ultrasound image UD to still image display and stops the scanning operation (step S105).

Upon completion of step S105, the controller 15 determines whether a contact operation is performed on the operation limit button Bda (step S106). If it is determined that a contact operation is performed on the operation limit button Bda (YES in step S106), the controller 15 shifts the operational mode of the ultrasound diagnosis apparatus 1 to the operation limit mode (step S115). Steps S106 and S115 are the same as steps S103 and S112, respectively.

The controller 15 determines whether an input operation is performed to instruct the saving of the ultrasound image UD (image saving operation) (step S116). In this case, if a predetermined push button of the operation input receiver 18 assigned to the saving of the ultrasound image UD is pushed, the controller 15 determines that the image saving operation is performed. Alternatively, the controller 15 may determine that an image saving operation is performed if a contact operation is performed on an operable button B corresponding to the save processing of the ultrasound image UD in the ultrasound diagnosis screen D.

If it is determined that an image saving operation is performed (YES in step S116), the controller 15 generates an image file for storage on the basis of the image data on the displayed ultrasound image UD and stores this image file in the HDD 152 (step S117). In specific, the controller 15 converts the image data on the ultrasound image UD to a predetermined file format, such as bitmap or JPEG, based on the image data on the first layer image D1, to generate image data for storage. The controller 15 adds predetermined additional information to the generated image data for storage to generate an image file containing, for example, image data in accordance with Digital Imaging and Communication in Medicine (DICOM) standard. The controller 15 stores the resulting image file in the HDD 152.

If step S117 is completed or if it is determined that the image saving operation is not performed in step S116 (NO in step S116), the controller 15 determines whether a contact operation is performed on the operation limit cancel button Ba (step S118). If it is determined that a contact operation is performed (YES in step S118), the controller 15 shifts the operational mode of the ultrasound diagnosis apparatus 1 to the normal mode (step S119), and the processing proceeds to step S109 described below. If it is determined that a contact operation is not performed (NO in step S118), the controller 15 continues to operate in the operation limit mode, and the processing proceeds to step S116. Steps S118 and S119 are the same as steps S113 and S114, respectively.

If it is determined that a contact operation is not performed on the operation limit button Bda in step S106 (NO in step S106), the controller 15 determines whether the image saving operation is performed (step S107). If it is determined that the image saving operation is performed (YES in step S107), the controller 15 generates an image file and stores this image file in the HDD 152 (step S108). Steps S107 and S108 are the same as steps S116 and S117, respectively.

If step S108 or S119 is completed or if it is determined that the image saving operation is not performed in step S107 (NO in step S107), the controller 15 determines whether a contact operation for instructing the freeze cancel processing (freeze cancel operation) is performed (step S109). In this case, if a contact operation is performed on the ultrasound image UD, the controller 15 determines that the freeze cancel operation is performed. If it is determined that the freeze cancel operation is performed (YES in step S109), the controller 15 resumes the scanning operation and switches the display of the ultrasound image UD to the moving image display (step S110). If it is determined that the freeze cancel operation is not performed (NO in step S109), the controller 15 proceeds the processing to step S106.

If step S110 is completed or if it is determined that the freeze operation is not performed in step S104 (NO in step S104), the controller 15 determines whether an input operation is input to the operation input receiver 18 to instruct the completion of the scanning operation (step S111). If it is determined that an input operation is not performed to instruct the completion of the scanning operation (NO in step S111), the controller 15 proceeds the processing to step S103. If it is determined that an input operation is performed to instruct the completion of the scanning operation (YES in step S111), the controller 15 ends the image file generation processing.

[First Modification]

A first modification of the embodiment described above will now be described. In this modification, the operable images, which correspond to processing carried out in response to contact operations, to be limited in the operation limit mode differ from those in the embodiment described above. The differences from the embodiment described above will now be described.

Figure 8:
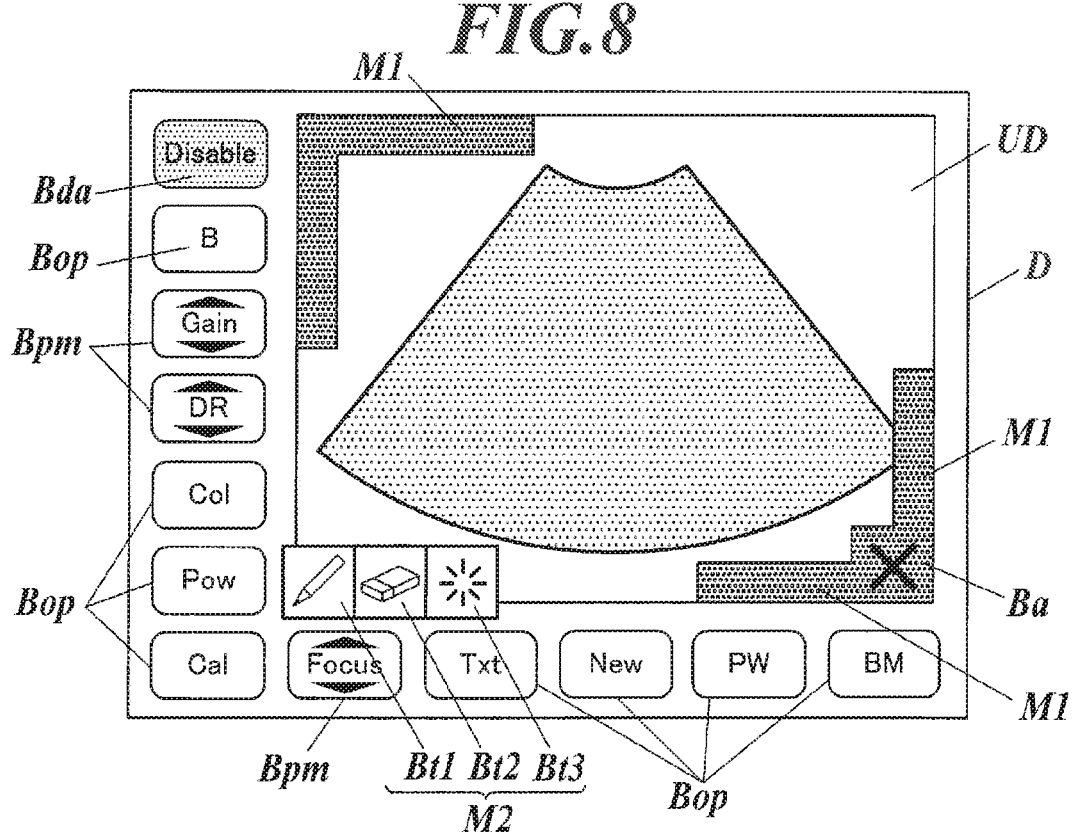
FIG. 8 illustrates an example ultrasound diagnosis screen in an operation limit mode according to a first modification.

FIG. 8 illustrates an example ultrasound diagnosis screen D in the operation limit mode according to the first modification. In the ultrasound diagnosis screen D according to this modification, the L-shaped operation-limit identification marks M1 appear at the upper left and lower right corners along the external edges of the ultrasound image UD, and the operation limit cancel button Ba overlays the operation-limit identification mark M1 at the lower right corner of the ultrasound image UD. In the case that only the contact operation of the ultrasound image UD is disabled and the contact operation of the operable buttons B is performed in the operation limit mode, the processing corresponding to the operable buttons B are carried out. In the operation limit mode, the trajectory of the contact operation is displayed in the form of a trajectory image T only within the area of the ultrasound image UD.

The second reference data of this modification contains the correspondence between the coordinate ranges of the operation limit cancel button Ba, the trajectory-processing-condition identification mark M2, and the operable buttons B and the processing to be carried out in response to contact operations of the respective coordinate ranges.

[Second Modification]

A second modification of the embodiment described above will now be described. In this modification, the processing carried out on the trajectory image T in the operation limit mode differs from that in the embodiment described above. The differences from the embodiment described above will now be described.

Figure 9:
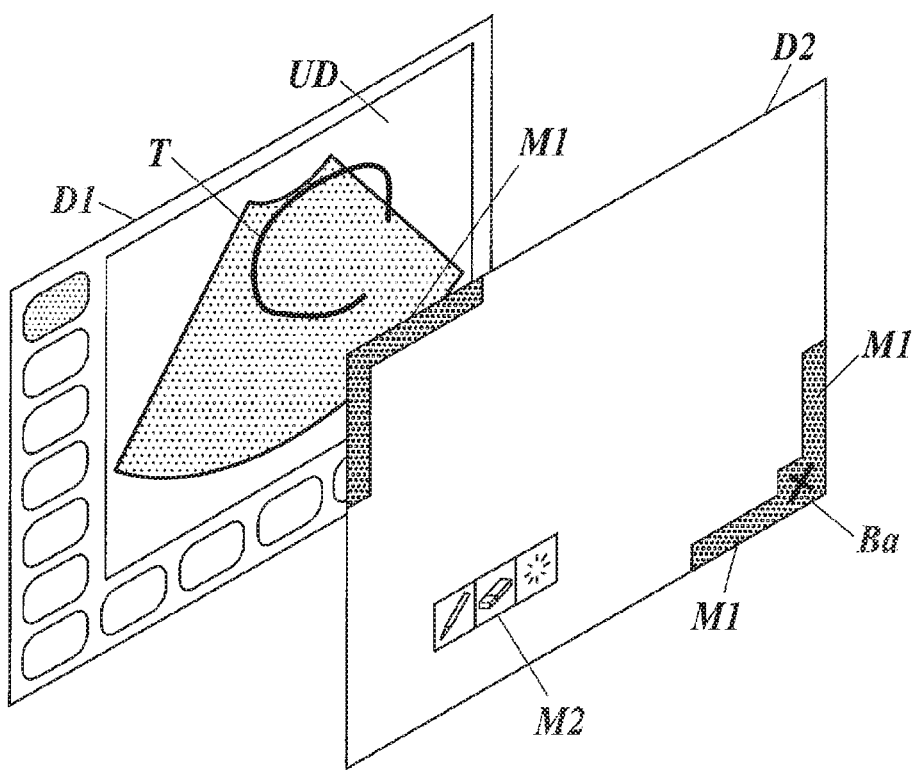
FIG. 9 illustrates layer images constituting an ultrasound diagnosis screen in an operation limit mode according to a second modification.

FIG. 9 illustrates layer images of the ultrasound diagnosis screen D in the operation limit mode according to the second modification.

In this modification, the image data on the trajectory image T is written over the image data on the first layer image D1, as illustrated in FIG. 9. In such a case, the image data on the first layer image D1 may be stored in the HDD 152 before the trajectory image T is written over so that the displayed trajectory image T can be deleted. In the case that the trajectory image T is deleted, the image data prior to the overwriting may be used for the display of the ultrasound diagnosis screen D.

The image data on the trajectory image T can be written over the image data on the first layer image D1 to store the ultrasound image UD including the trajectory image T through simple processing.

[Third Modification]

A third modification of the embodiment described above will now be described. In the embodiment described above, the trajectory image T can be displayed in the operation limit mode. Such display of the trajectory image T may be omitted, if unnecessary. If the display is omitted, the display of the trajectory-processing-condition identification mark M2 is also omitted.

Alternatively, contact operations of the entire ultrasound diagnosis screen D (i.e., the entire touch panel 19B) may be disabled, without display of the operation limit cancel button Ba in the operation limit mode. In such a case, the normal mode cannot be resumed by ending the operation limit mode through a contact operation of the touch panel 19B. Thus, the operation limit mode may be ended by, for example, performing a predetermined input operation of the operation input receiver 18 and determining that the operation limit condition is no longer satisfied.

[Fourth Modification]

A fourth modification of the embodiment described above will now be described. This modification differs from the embodiment described above in that the positions of the operable buttons B and the ultrasound image UD can be customized. The differences from the embodiment described above will now be described.

The ultrasound diagnosis apparatus 1 according to this modification can shift to a customizing mode for adjusting the positions and sizes of the operable buttons B and the ultrasound image UD in response to predetermined input operations of the operation input receiver 18 or the touch panel 19B by an operator. In the customizing mode, the positions and sizes of the operable buttons B and the ultrasound image UD in the ultrasound diagnosis screen D can be freely adjusted or varied in response to input operations of the operation input receiver 18 and the touch panel 19B by an operator, if the visibility of the ultrasound image UD is unaffected. Also, the type of operable buttons B to be displayed may be selected.

Figure 10A:
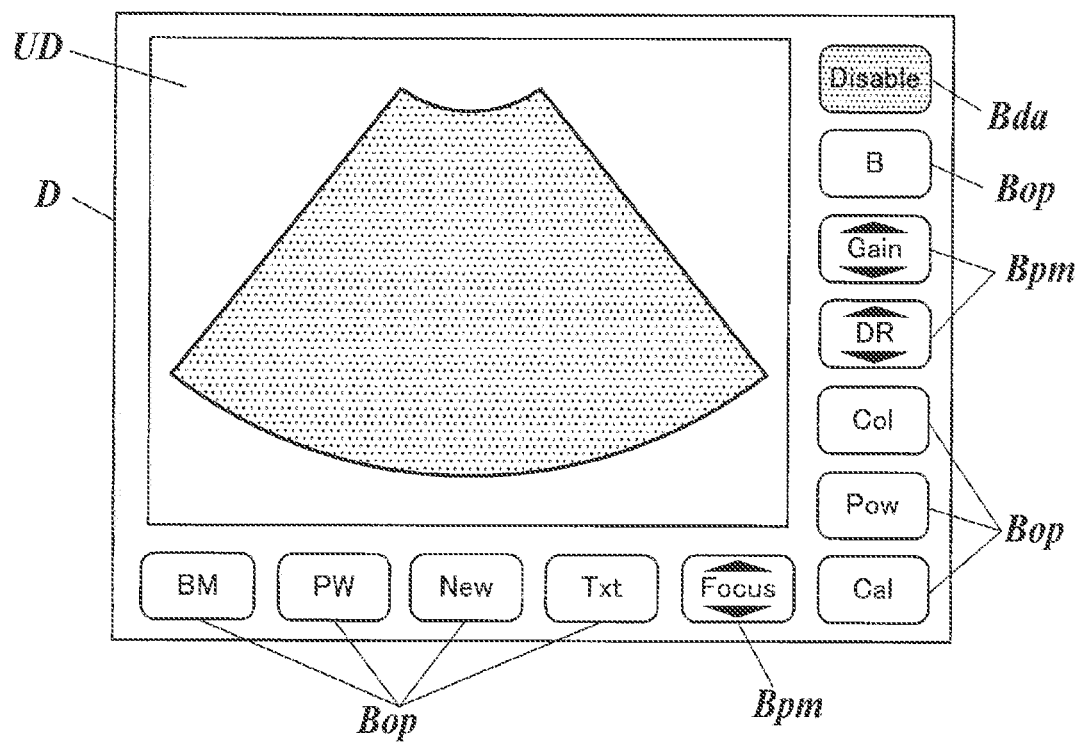
FIGS. 10A and 10B illustrate example arrangements of operable buttons in ultrasound diagnosis screens according to a fourth modification.
Figure 10B:
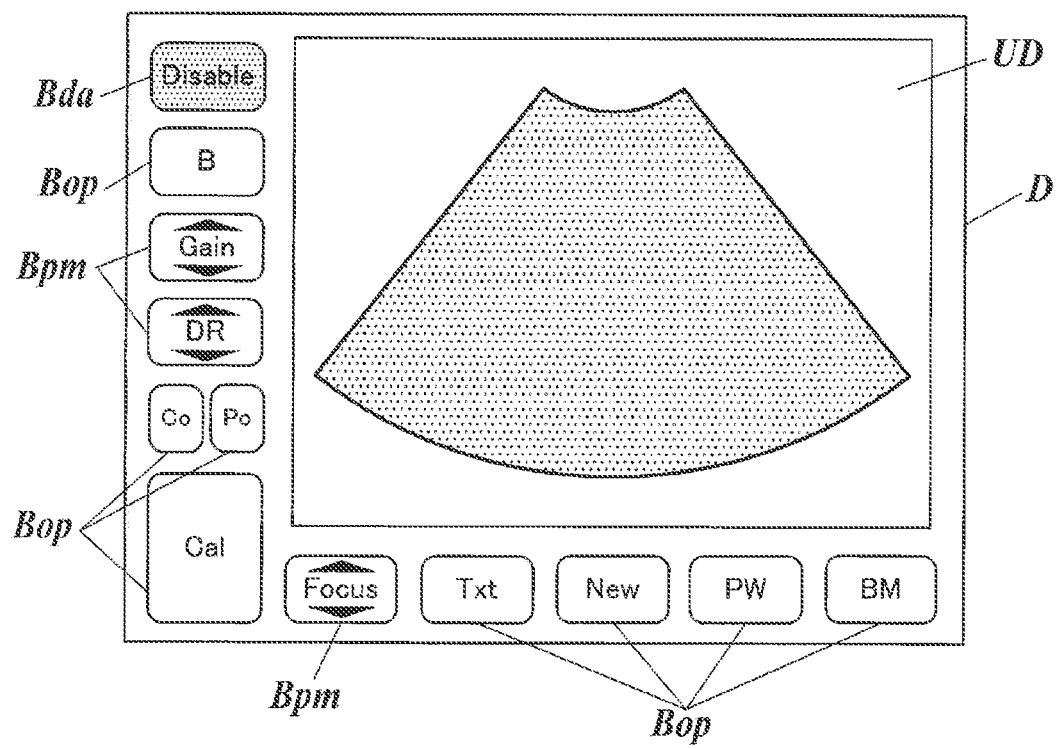

FIGS. 10A and 10B illustrate example positions of the operable buttons B in the ultrasound diagnosis screen D according to the fourth modification.

FIG. 10A illustrates the ultrasound diagnosis screen D customized such that the positions of the operable buttons B are symmetrical to those in FIG. 3. Such customization allows the operator to select, for example, one of the positions of the operable buttons B in FIGS. 3 and 10A depending on the dominant hand of the operator.

FIG. 10B illustrates the ultrasound diagnosis screen D customized such that some of the operable buttons B are enlarged or micrified. The operable buttons B that are frequently used can be enlarged depending on the diagnosis applied by the operator, to enhance operability and diagnosis efficiency. The operable buttons B that are infrequently used can be micrified to provide space for other operable buttons B or to display more operable buttons B.

The positional regions of the operable buttons B are not limited to those illustrated in FIGS. 10A and 10B. For example, in place of the L-shaped region, the operable buttons B may be collectively disposed along one side of the ultrasound diagnosis screen D or along three sides of the ultrasound diagnosis screen D.

Alternatively, the sizes and the positions of the operable buttons B may be automatically determined by the controller 15. In such a case, the importance and type of the operable buttons B to be displayed may be preliminarily identified by the operator, and the controller 15 may automatically customize the operable buttons B under these conditions. As illustrated in FIG. 11, the correspondence between multiple diagnosis targets and positioning patterns of the operable buttons B may be preliminarily established so that the positions of the operable buttons B are automatically changed in accordance with the diagnosis target (examination target) selected by the operator through an input operation (step S101 in FIG. 7). In the example illustrated in FIG. 11, the positioning patterns of the operable buttons B for the diagnosis targets of an abdominal site, an obstetric site, a gynecologic site, a thyroid site, a carotid artery, and an orthopedic site are patterns A, B, B, C, D, and E, respectively.

As described above, the ultrasound diagnosis apparatus 1 according to this embodiment includes an ultrasound probe 20 that radiates ultrasounds toward the inside of a subject, receives reflected waves from the subject, and converts the received waves to an ultrasound image UD; a display 19A having a screen that displays the ultrasound image UD and a touch panel 19B overlaid on the screen; and a controller 15. The controller 15 of the ultrasound diagnosis apparatus 1 causes operable buttons B and the ultrasound image UD that are operable images to appear on the display 19A to indicate a target of a contact operation in the touch panel 19B overlaying the screen of the display 19A (image display controller); carries out predetermined processing corresponding to the operable buttons B and the ultrasound image UD in response to the contact operation of the touch panel 19B (processor); and skips the predetermined processing corresponding to the at least some of the operable buttons B and ultrasound image UD if a predetermined operation limit condition is satisfied (processor).

Such a configuration can prevent false operation due to unintentional contact with the touch panel 19B when an operator operates the screen of the display 19A. In this way, a reduction in the diagnosis efficiency due to operations required for recovery from the false operation can be avoided and the load of the recovery operation on the operator can be reduced. Since the operator can operate the screen of the display 19A without extra caution for preventing false operation, appropriate diagnosis can be unlimitedly conducted with the display 19A of the ultrasound diagnosis apparatus 1.

If the ultrasound image UD appears on the display 19A in the form of an operable image (image display controller) and the operation limit condition is satisfied, the controller 15 skips the processing corresponding to at least the ultrasound image UD (processor). This can prevent false operations that occur when the operator operates the ultrasound image UD on the screen.

If the operation limit button Bda (image display controller) appears on the display 19A in the form of an operable image on the display 19A and an input operation is performed to the operation limit button Bda on the touch panel 19B, the controller 15 determines that the operation limit condition is satisfied (processor). This can shift the operational mode to the operation limit mode in accordance with the contact operation of the operation limit button Bda performed by the operator. Thus, contact operations of the touch panel 19B, such as operation of the screen, can be limited in accordance with the intent of the operator. This can more appropriately restrict the operation of the touch panel 19B.

If the operation limit condition is satisfied, the controller 15 causes the operation limit cancel button Ba to appear on the display 19A in the form of an operable image (image display controller). If an input operation of the operation limit cancel button Ba is performed on the touch panel 19B, the controller 15 determines that the operation limit condition is no longer satisfied (processor). This can end the operation limit mode in response to a contact operation of the operation limit cancel button Ba by the operator and enter the normal mode. Thus, the operator can cancel the restriction on contact operations of the touch panel 19B to perform normal contact operations of the operable buttons B and the ultrasound image UD. In this way, contact operations can be satisfactorily restricted in accordance with the intent of the operator.

If the operation limit condition is satisfied, the controller 15 skips the processing corresponding to the operable images other than the operation limit cancel button Ba (processor). This causes only the operation limit cancel button Ba, which is operated to resume the normal mode, to be activated in the operation limit mode. Thus, a false operation due to unintentional contact with the touch panel 19B can be more certainly prevented.

If the operation limit condition is satisfied, the controller 15 skips the processing corresponding to all of the operable buttons B and the ultrasound image UD (processor). This can more certainly prevent false operations due to unintentional contact with the touch panel 19B.

If the operation limit condition is satisfied, the controller 15 causes a trajectory image T that indicates at least a portion of the trajectory of the contact operation performed to the touch panel 19B to appear on the display 19A (trajectory display controller). This can achieve readily comprehensible diagnosis using the trajectory image T of a contact operation.

If the operation limit condition is satisfied, the controller 15 causes a trajectory-processing-condition identification mark M2 indicating the display of the trajectory image T to appear on the display 19A (image display controller). This enables the operator to readily determine whether the trajectory of a contact operation is to appear in the form of a trajectory image T.

If the operation limit condition is satisfied, the controller 15 causes the partial-trajectory deletion button Bt2 and the full-trajectory deletion button Bt3 corresponding to the trajectory deletion processing pertaining to the deletion of the trajectory image T to appear on the display 19A (image display controller). If an input operation is performed to the partial-trajectory deletion button Bt2 or the full-trajectory deletion button Bt3 on the touch panel 19B, the controller 15 carries out the trajectory deletion processing to delete part or all of the trajectory image T from the image appearing on the display 19A (trajectory display controller). This can provide flexible assistance and/or supplementary information for the diagnosis through the trajectory image T.

If the operation limit condition is satisfied, the operation-limit identification marks M1 indicating that the processing corresponding to at least some of the operable buttons B and ultrasound image UD is skipped appear on the display 19A (image display controller). In this way, the operator can readily determine whether the trajectory of the contact operation is to be displayed in the form of a trajectory image T. The operator can also readily determine whether contact operations restricted for at least some of the operable buttons B and the ultrasound image UD.

The controller 15 stores the image data corresponding to images appearing on the display 19A from which at least the trajectory image is removed, in the HDD 152 (storage controller). In this way, the image data on the original image of the ultrasound image UD not including the trajectory image T used for the assistance and/or supplementary information of the diagnosis can be stored through simple processing.

The controller 15 stores the image data corresponding to image appearing on the display 19A from which at least the operation-limit identification marks M1 are removed, in the HDD 152 (storage controller). In this way, the image data on the original ultrasound image not including the operation-limit identification marks M1, which is used as an indicator involving operation limit for the operator, can be stored through simple processing.

If the operation limit condition is satisfied, the controller 15 causes a combined image of the first layer image D1 including the operable buttons B and the ultrasound image UD overlaid with the second layer image D2 different from the first layer image D1 to appear on the display 19A (image display controller) and carries out predetermined processing selected in accordance with the position of the contact operation performed to the touch panel 19B in the second layer image (processor). In this way, the processing corresponding to the contact operation is selected based on the second layer image in the operation limit mode, so that processing corresponding to contact operations of the operable buttons B and the ultrasound image UD can be readily prevented from being carried out.

If the operation limit condition is satisfied, the controller 15 causes the trajectory image T including at least part of the trajectory of the contact operation performed on the touch panel 19B to appear on the display 19A as part of the second layer image D2 (trajectory display controller). In this way, the image data on the ultrasound image UD included in the first layer image D1 can be stored without the trajectory image T.

If the operation limit condition is satisfied, the controller 15 according to the second modification causes the trajectory image T including at least part of the trajectory of the contact operation performed on the touch panel 19B to appear on the display 19A as part of the first layer image D1 (trajectory display controller). In this way, the image data on the ultrasound image UD included in the first layer image D1 can be stored with the trajectory image T written thereover.

If the operation limit condition is satisfied, the controller 15 causes the trajectory-processing-condition identification mark M2 indicating that the trajectory image T is to be displayed to appear on the display 19A as part of the second layer image D2 (image display controller). In this way, the image data on the ultrasound image UD of the first layer image D1 can be stored without the trajectory-processing-condition identification mark M2.

If the operation limit condition is satisfied, the controller 15 causes the partial-trajectory deletion button Bt2 and the full-trajectory deletion button Bt3 corresponding to the trajectory deletion processing pertaining to deletion of the trajectory image T to appear on the display 19A as part of the second layered image D2 (image display controller). If an input operation is performed to the partial-trajectory deletion button Bt2 or the full-trajectory deletion button Bt3 on the touch panel 19B, the controller 15 carries out the trajectory deletion processing to delete part or all of the trajectory image from the image on the display 19A (trajectory display controller). In this way, the image data on the ultrasound image UD of the first layer image D1 can be stored without the partial-trajectory deletion button Bt2 and the full-trajectory deletion button Bt3.

If the operation limit condition is satisfied, the controller 15 causes the operation-limit identification marks M1 indicating that the processing corresponding to at least some of the operable buttons B and the ultrasound image UD are to be skipped to appear on the display 19A as part of the second layered image D2 (image display controller). In this way, the image data on the ultrasound image UD of the first layer image D1 can be stored without the operation-limit identification marks M1.

The controller 15 stores the image data on a portion of the first layer image D1 including at least the ultrasound image UD in the HDD 152 (storage controller). In this way, the ultrasound image UD can be stored without components of the second layer image D2 through simple processing.

The ultrasound diagnosis apparatus 1, which includes the HDD 152, can store the ultrasound image UD therein.

Since the ultrasound diagnosis apparatus 1 includes the display 19A and the touch panel 19B, the standalone ultrasound diagnosis apparatus 1 can display various images and perform contact operations.

The programs according to this embodiment permits a computer provided in the ultrasound diagnosis apparatus 1 to function as an image display controller that causes operable buttons B and the ultrasound image UD that are operable images to appear on the display 19A to indicate a target of a contact operation in the touch panel 19B overlaying the screen of the display 19A; and a processor that carries out predetermined processing corresponding to the operable buttons B and the ultrasound image UD in response to the contact operation of the touch panel 19B, wherein the processor skips the predetermined processing corresponding to the at least some of the operable buttons B and ultrasound image UD if a predetermined operation limit condition is satisfied. Such a configuration can prevent false operation due to unintentional contact with the touch panel 19B when an operator operates the screen of the display 19A.

The present invention should not be limited to the embodiments and modifications described above and may include various other modifications.

For example, in the embodiments and modifications described above, the normal mode and the operation limit mode are switched through contact operations of the operation limit button Bda and the operation limit cancel button Ba by the operator. Any other switching mode is also available in the present invention. Alternatively, the operational mode may be shifted from the normal mode to the operation limit mode in accordance with the processing carried out by the controller 15. That is, the operation limit condition may be satisfied when the controller 15 proceeds to a predetermined step in the processing. As an example of such a configuration, the operational mode may automatically shift to the operation limit mode upon start of the scanning operation and display of the ultrasound diagnosis screen D including the ultrasound image UD on the display 19A. In such a case, the operational mode can return from the operation limit mode to the normal mode in response to a contact operation of the operation limit cancel button Ba or a predetermined input operation (for example, a freeze operation or an image saving operation) of the operation input receiver 18 by the operator.

In the embodiments and modifications described above, the processing corresponding to the operable buttons B and the ultrasound image UD are determined to be carried out based on the coordinates of the contact operations indicated by operational signals sent from the touch panel 19B to the controller 15 in the operation limit mode. However, the present invention should not be limited thereto. Alternatively, a touch panel controller that controls the output of the operational signals from the touch panel 19B may be provided. In this way, operational signals corresponding to contact operations of the touch panel 19B in regions in which contact operations are limited can be prevent from being sent to the controller 15 in the operation limit mode, so that the processing corresponding to the operable buttons B and the ultrasound image UD are not carried out. In such a case, the touch panel controller and the controller 15 constitute the processor.

In the embodiments and the modifications described above, the operable buttons B and the ultrasound image UD exemplify operable images. However, any other operable image is also available. For example, the operable images include any images that receive contact operations to carry out predetermined processing, such as images of keys of a software keyboard, checkboxes, radio buttons, slider bars, and dropdown lists displayed on the ultrasound diagnosis screen D.

In the embodiments and the modifications described above, the operation limit cancel button Ba or operation limit image is displayed as one of the multiple operable buttons B. Any other display state of the operation limit image is also available. For example, an independent operation limit cancel button Ba may be displayed in a size and at a position readily visible to the user outside the positional region of the operable buttons B.

In the above example, two L-shaped operation-limit identification marks M1 or operation-limit identification images are displayed. However, the operation-limit identification marks M1 should not be limited thereto. The operation-limit identification images may be any images that can inform the user that the contact operation of the touch panel 19B is limited. For example, an image of a frame outlining the four sides of the ultrasound diagnosis screen D may be displayed, or images including texts messages and warning signs indicating that the contact operation is limited may appear at a position readily visible by the user (for example, near the ultrasound image UD).

In the example described above, the operation limit cancel button Ba or operation limit cancel image overlays the operation-limit identification marks M1. Any other display state of the operation limit cancel image is also available. For example, the operation limit cancel button Ba may be one of the operable buttons B.

In the embodiments and the modifications described above, the present invention is applied to an ultrasound diagnosis apparatus 1 including an operational display 19 and an ultrasound probe 20. Alternatively, the present invention may be applied to an ultrasound diagnosis apparatus including an ultrasound diagnosis apparatus body 10 that is detachable from at least one of the operational display 19 and the ultrasound probe 20.

In the embodiments and the modifications described above, the HDD 152 exemplifies a computer readable recording medium that stores programs. Any other computer readable recording medium is also available. The computer readable recording medium may be a portable recording medium, such as a flash memory or a CD-ROM, besides the HDD 152 and a solid-state drive (SSD).

The embodiments described above should not be construed to limit the present invention, and the claims and other equivalents thereof are included in the scope of the invention.

Although embodiments of the present invention have been described and illustrated in detail, it is clearly understood that those are mere examples, and the scope of the present invention should not be limited to the examples in the descriptions and the appended claims.

What is claimed is:

1. An ultrasound diagnosis apparatus which generates an ultrasound image based on a reception signal obtained by an ultrasound probe to display the ultrasound image in a display, the reception signal being of ultrasound transmitted from the ultrasound probe toward an inside of a subject and reflected at the inside of the subject, the apparatus comprising:
    a display and a touch panel that overlays a display screen of the display;
    an image display controller that causes the display to display at least one operable image including a predetermined operation limit image, the at least one operable image indicating a target of a contact operation in the touch panel provided on the display screen of the display; and
    a processor that carries out predetermined processing corresponding to the at least one operable image as the target of the contact operation in response to the contact operation in the touch panel,
    wherein the processor determines that the operation limit condition is satisfied when an input operation is performed at the operation limit image in the touch panel and the processor skips the predetermined processing corresponding to each of the at least one operable image when the input operation is performed at the operation limit image in the touch panel and the processor determines that the operation limit condition is satisfied.

2. The ultrasound diagnosis apparatus of claim 1, wherein the image display controller causes the display to display the ultrasound image as one of the at least one operable image, and
    the processor skips the predetermined processing corresponding to at least the ultrasound image when the operation limit condition is satisfied.

3. The ultrasound diagnosis apparatus of claim 1, wherein the image display controller causes the display to display a predetermined operation limit cancel image when the operation limit condition is satisfied, and
    the processor determines that the operation limit condition is no longer satisfied when an input operation is performed at the operation limit cancel image in the touch panel.

4. The ultrasound diagnosis apparatus of claim 3, wherein the image display controller causes the display to display an operation-limit identification image indicating that the predetermined processing corresponding to the predetermined operable image is skipped when the operation limit condition is satisfied.

5. The ultrasound diagnosis apparatus of claim 4, further comprising:

a storage controller that stores, in a storage, image data of the image displayed in the display from which at least the operation-limit identification image is removed.

6. The ultrasound diagnosis apparatus of claim 1, further comprising:
a trajectory display controller that causes the display to display a trajectory image indicating at least part of a trajectory of the contact operation in the touch panel when the operation limit condition is satisfied.

7. The ultrasound diagnosis apparatus of claim 6, wherein the image display controller causes the display to display a trajectory-display-state identification image indicating that the trajectory image is displayed when the operation limit condition is satisfied.

8. The ultrasound diagnosis apparatus of claim 6, wherein the image display controller causes the display to display a trajectory deletion image corresponding to a trajectory deletion processing pertaining to deletion of the trajectory image when the operation limit condition is satisfied, and
the trajectory display controller carries out the trajectory deletion processing to delete part or all of the trajectory image from the display when an input operation is performed at the trajectory deletion image in the touch panel.

9. The ultrasound diagnosis apparatus of claim 6, further comprising:
a storage controller that stores, in a storage, image data of the image displayed in the display from which at least the trajectory image is removed.

10. The ultrasound diagnosis apparatus of claim 9, further comprising:
the storage.

11. A non-transitory computer readable recording medium storing a program, the medium being readable by a computer provided in an ultrasound diagnosis apparatus which generates an ultrasound image based on a reception signal obtained by an ultrasound probe to display the ultrasound image in a display, the reception signal being of ultrasound transmitted from the ultrasound probe toward an inside of a subject and reflected at the inside of the subject, the program causing the computer to function as:
an image display controller that causes the display to display at least one operable image including a predetermined operation limit image, the operable image indicating a target of a contact operation in a touch panel provided so as to be overlaid on a display screen of the display; and
a processor that carries out predetermined processing corresponding to the operable image as the target of the contact operation in response to the contact operation in the touch panel,
wherein the processor determines that the operation limitation condition is satisfied when an input operation is performed at the operation limit image in the touch panel and the processor skips the predetermined processing corresponding to each the at least one operation image when the input operation is performed at the operation limit image in the touch panel and the processor determines that the operation limitation condition is satisfied.

12. An ultrasound diagnosis apparatus which generates an ultrasound image based on a reception signal obtained by an ultrasound probe to display the ultrasound image in a display, the reception signal being of ultrasound transmitted from the ultrasound probe toward an inside of a subject and reflected at the inside of the subject, the apparatus comprising:
a display and a touch panel that overlays a display screen of the display;
an image display controller that causes the display to display at least one operable image indicating a target of a contact operation in the touch panel provided on the display screen of the display;
a processor that carries out predetermined processing corresponding to the at least one operable image as the target of the contact operation in response to the contact operation in the touch panel,
wherein the processor skips the predetermined processing corresponding to a predetermined operable image among the operable image when a predetermined operation limit condition is satisfied; and
a trajectory display controller, wherein the image display controller causes the display to display a trajectory-processing-condition identification mark including a trajectory-display-state identification image and a trajectory deletion image when the predetermined operation limit is satisfied, the trajectory display controller causes at least part of a trajectory image of a trajectory of the contact operation in the touch panel to be displayed when an input operation is performed at the trajectory-display-state identification image and the trajectory display controller causes deletion of at least part of the trajectory image on the display when an input operation is performed at the trajectory deletion image.

* * * * *